United States Patent [19]

Tachibana et al.

[11] Patent Number: 4,901,862

[45] Date of Patent: Feb. 20, 1990

[54] INSPECTION APPARATUS FOR FLANGED OR CURLED OPEN END PARTS OF CANS

[75] Inventors: Shigeru Tachibana, Takaoka; Minoru Takegoshi; Takashi Danzuka, both of Toyama, all of Japan

[73] Assignee: Takeuchi Press Industries Co., Ltd., Toyama, Japan

[21] Appl. No.: 241,429

[22] Filed: Sep. 7, 1988

[30] Foreign Application Priority Data

May 12, 1988 [JP] Japan .................... 63-115543

[51] Int. Cl.[4] .......................... B07C 5/344
[52] U.S. Cl. ...................... 209/567; 209/571; 209/912
[58] Field of Search ........... 209/529, 588, 597, 905, 209/912, 567, 570, 571

[56] References Cited

U.S. PATENT DOCUMENTS

| | | | |
|---|---|---|---|
| 3,392,829 | 7/1968 | Keinanen | 209/529 |
| 3,465,878 | 9/1969 | Ochs | 209/570 X |
| 4,074,809 | 2/1987 | McMillin et al. | 209/588 |
| 4,105,122 | 8/1978 | Flood et al. | 209/588 X |
| 4,385,699 | 5/1983 | Ashina | 209/538 |
| 4,455,225 | 6/1984 | Morimoto et al. | 209/912 X |
| 4,579,227 | 4/1986 | Miller | 209/588 X |
| 4,641,092 | 2/1987 | Sakamoto et al. | 324/240 X |
| 4,703,859 | 11/1987 | Pynsky | 209/597 |

FOREIGN PATENT DOCUMENTS

| | | |
|---|---|---|
| 54-124781 | 9/1979 | Japan . |
| 56-54350 | 5/1981 | Japan . |
| 58-139052 | 8/1983 | Japan . |
| 59-20977 | 5/1984 | Japan . |
| 59-87303 | 5/1984 | Japan . |

Primary Examiner—Margaret A. Focarino
Assistant Examiner—Gary C. Hoge
Attorney, Agent, or Firm—Armstrong, Nikaido, Marmelstein, Kubovcik & Murray

[57] ABSTRACT

An inspection apparatus for flanged or curled part of can having a cylindrical body and an open end comprising a feeding means, a holding means, an inspecting means, a locating means, a discriminating means and a discharging means, wherein the inspection is carried out continuously. According to the present invention, visual inspection falls into disuse, and inspection efficiency is improved.

1 Claim, 7 Drawing Sheets

INSPECTION APPARATUS FOR FLANGED OR CURLED OPEN END PARTS OF CANS

BACKGROUND OF THE INVENTION

The present invention relates to an inspection apparatus for flanged or curled open end parts of cans, and more particularly to an inspection apparatus for flanged or curled open end parts of cans wherein the inspection can be carried out continuously.

Hitherto, as inspection methods for flanged parts of deep drawn cans and curled parts of aerosol cans, made of metal plate such as tin plate, aluminum plate and tin free steel plate, there are known an air tester method and an optical tester method.

Figure 6:
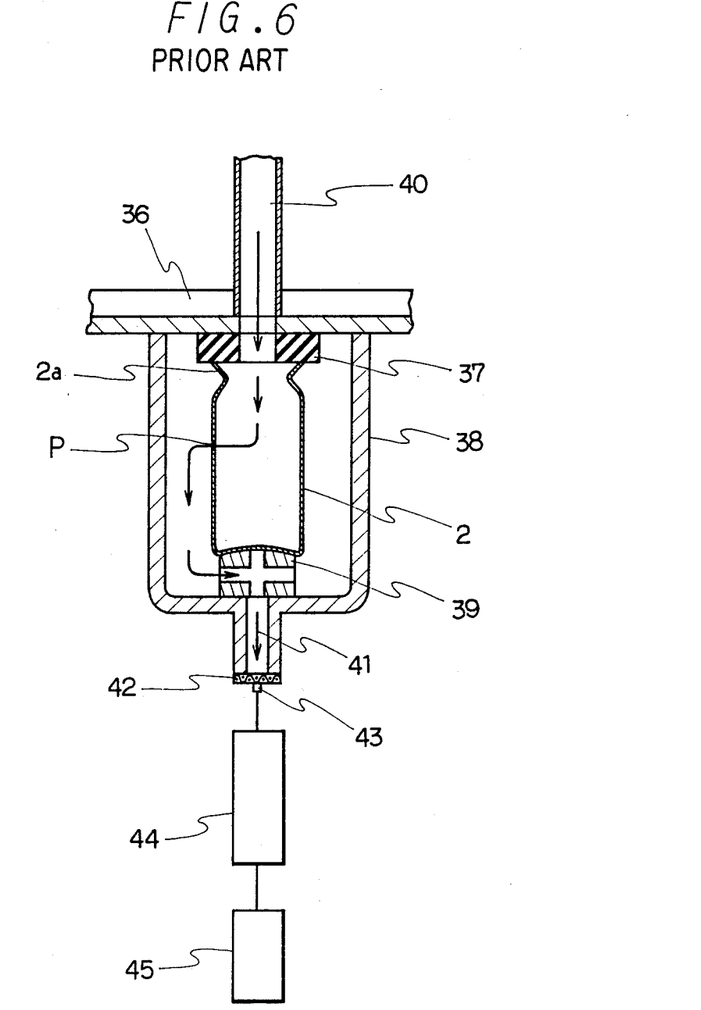
FIG. 6 shows an explanatory view of a conventional air tester method for flanged or curled parts of cans.

According to the air tester method, detection of defects is carried out as shown in FIG. 6. The procedure is explained by the following (a) to (e).

(a) An open end of a can 2 is pressed onto rubber material 37 on substrate 36 by a pusher 39 contained in a sealed tube 38.

(b) Compressed air having a positive pressure of about 0.6 kg/cm$^2$ is supplied continuously inside of the can through an air pipe 40.

(c) If the can has a pin hole p, air leaks through the pin hole p and flows to the outlet of the inspection nozzle.

(d) The air flow is detected via vibration of wire mesh 42 or differential pressure by a sensor 43.

(e) The signal from the sensor 43 is transmitted to a detector 45 via an amplifier 44, and then the defect of flanged part 2a or curled part 2b is detected by the level of signal.

Figure 7:
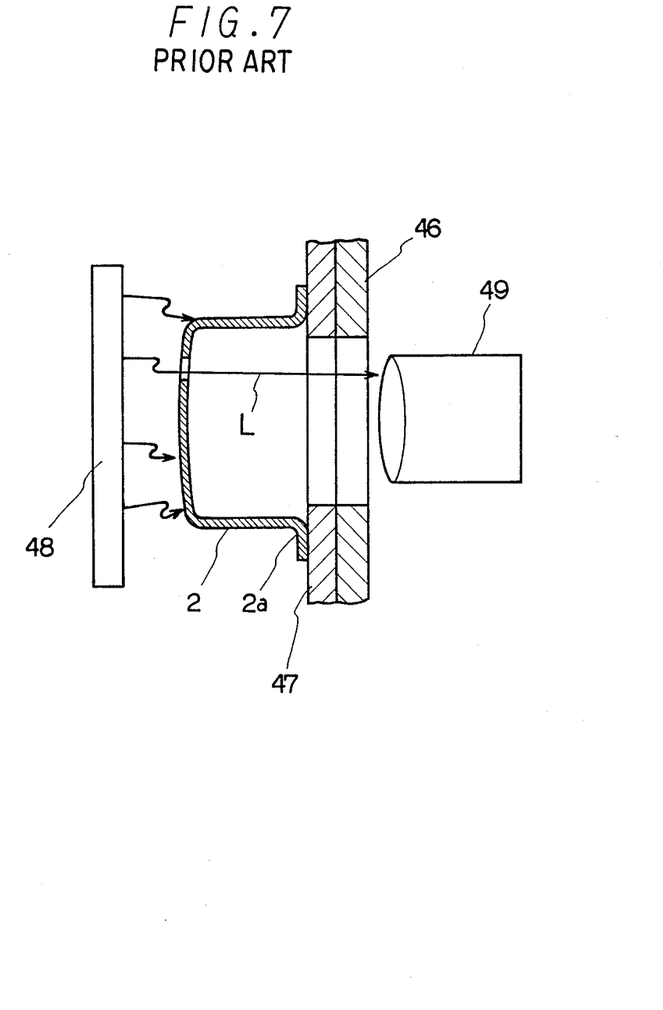
FIG. 7 shows an explanatory view of a conventional optical tester method for flanged or curled parts of cans.

According to the optical tester method, detection of defects is carried out as shown in FIG. 7. The procedure is explained by the following (a) to (d).

(a) A can 2 is stuck onto rubber material 47 on substrate 46 by suction.

The suction, for example, can be done by making negative pressure inside of the can 2.

(b) The can 2 is irradiated by a light source 48.

(c) If the can 2 has any pin hole, light leaks through the pin hole.

(d) The leaking light L is detected by a photo detector 49 such as photo multiplier tube, and then the defects of flanged part 2a or curled part 2b are detected.

Since both conventional methods as mentioned above can display their ability when the flange part 2a or the curled part 2b of can 2 is stuck onto rubber material 37 or 47, they can only detect such defects as reach to the body of can 2. However, they cannot detect small cracks of the flanged part or curled part. Therefore, after the cans 2 are inspected by the air tester method and the like, all of them are visually inspected by specially arranged inspectors. However, oversight of defects easily occurs during visual inspection. Small defects, which are not discriminated by visual inspection, cannot be detected either. It takes too long to inspect the can by the visual inspection. In result, the visual inspection has become non efficient and the main bottleneck of can production line.

Japanese Examined Patent Publication No. 20977/1984 discloses an inspection apparatus for a flanged part of cans which solves the problems of the conventional tester methods by automatically rejecting cans with defects. Namely, it provides a flange crack tester for two piece can comprising;

(a) a vertically arranged can feeding mechanism having a vertically arranged timing screw which horizontally arranges cans in line and intermittently transfers cans one by one and a non-contact sensor closely facing one end of a timing plate attached firmly on an infeed driving shaft which is connected to one end of timing screw with synchronously drivable condition via bevel gear, places cans, which are fed continuously on a can feeding station, one by one to the prescribed position in static magnetic field of inspection station, (b) a rotary mechanism which forcibly rotates cans, wherein the can is held in the prescribed position in the inspection station, and is supported horizontally by outside body thereof, without applying force in longitudinal direction, and with driving torque being directly transmittable, (c) a magnetic head closely facing a part of a flanged part of can which is rotated in the inspection station, (d) a discriminating circuit detecting cans with defects, wherein the magnetic head output signal, which indicates the inspected part condition, is transmitted to a wave form modification circuit which applifies and shapes the signal, and then the signal is compared with a standard signal stored previously, and (e) a rejector which rejects cans with defects during inspection by allowing them to fall by self-weight, by receiving a discriminating circuit operational signal which is controlled by a timing signal from the timing screw.

According to the above-mentioned flange crack tester, high speed inspection can be realized without applying undue force to cans to be inspected.

However, it is obliged that the inspection becomes intermittent since the flanged part of the can is inspected by a fixed sensor in a condition that the revolution of can is stopped at the prescribed position and then the can is forcibly rotated. In addition, the number of sensor is one, therefore, the inspection efficiency is very low. In result, the apparatus has a defect that it cannot improve in the inspection efficiency of the can production line enough.

It is an object of the present invention to solve the above mentioned problems of the conventional inspection apparatus, i.e., to provide an inspection apparatus wherein visual inspection falls into disuse, the inspection for the flanged or curled part of cans can be carried out continuously without stopping cans, and the inspection efficiency is improved.

SUMMARY OF THE INVENTION

An inspection apparatus for flanged or curled parts of cans of the present invention is concerned with an inspection apparatus inspecting flanged or curled parts of cans having a cylindrical body and an opening comprising;

(a) a feeding means which feeds cans continuously, (b) a holding means which removably holds a can fed by the feeding means, (c) an inspecting means which inspects a flanged or curled part of the can, (d) a locating means which keeps the sensor holders at a certain location relative to the flanged or curled part of can, (e) a discriminating means which discriminates if there is any defect in flanged or curled part by information from the inspecting means, and (f) a discharging means which discharges a can with defects at a prescribed position, and a can without defects at another prescribed position respectively.

In an embodiment, the inspecting means has plural sensors and plural sensor holders facing the flanged or curled open end part of cans.

The inspection apparatus for flanged or curled open end parts of cans of the present invention enables the inspection to be carried out by the inspecting means when the can is moving, so that the visual inspection for flanged or curled parts falls into disuse, and the inspection is carried out continuously.

DETAILED DESCRIPTION

Referring now to the drawings for more complete understanding of the present invention, there is explained an inspection apparatus for flanged or curled open end parts of cans.

Figure 1:
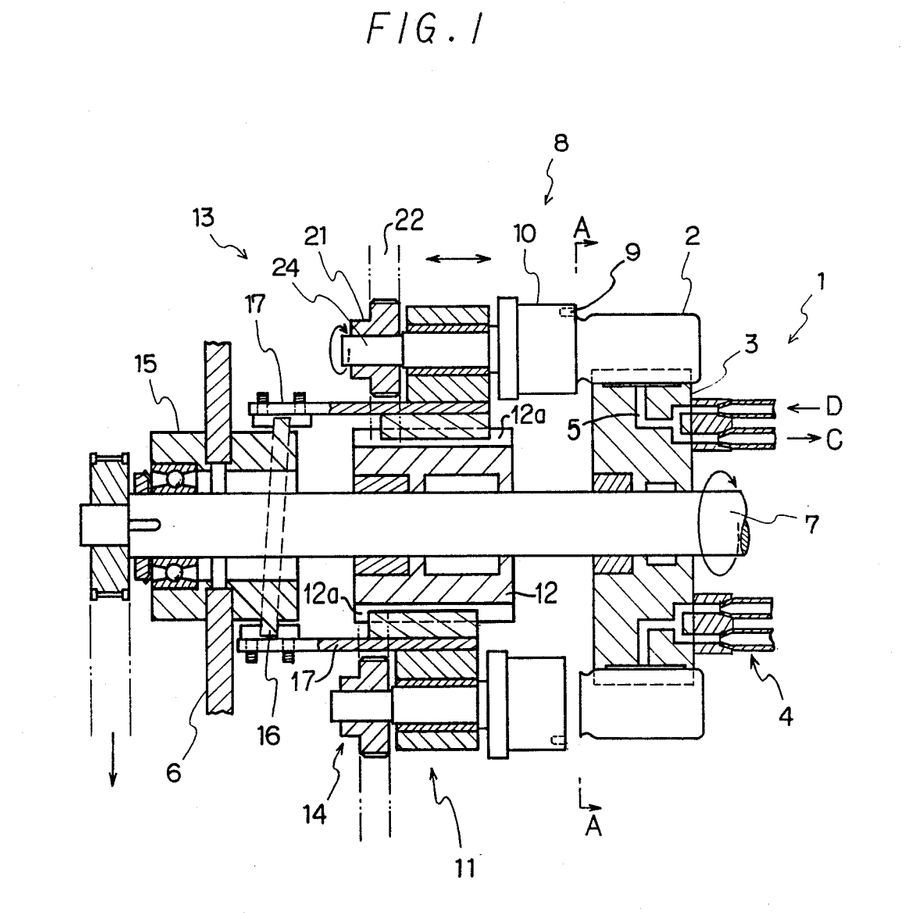
FIG. 1 shows a longitudinal sectional view of an embodiment of an inspection apparatus for flanged or curled open end parts of cans of the present invention.

FIG. 1 shows a longitudinal sectional view of an embodiment of an inspection apparatus for flanged or curled parts of cans of the present invention;

In FIG. 1, a holding means 1 has a receiving element 3 which has desired numbers of receivers, wherein cans 2 are delivered by delivering means (not shown) along outer circle of the receiver, and a holding means 4 which holds the cans 2 with easy removal. The receivers of the receiving element 3 have concave surfaces. The concave surfaces are covered with the can 2 when the can 2 is placed. The concave has an opening for a passage 5 which branches into two passages inside of the receiving element 3.

The branching passages are opened at the same vertical end of the element 3 respectively, and are communicated with a flow switching device (not shown) of the holding means 4 respectively. Holding and releasing of each can 2 is carried out by changing internal pressure of the concave by means of the holding means 4. Namely, when holding of can 2 is required, the internal pressure of the concave is made less than the atmospheric pressure by exhausting the internal air thereof (as shown in FIG. 1 by arrow C) by means of the flow switching device. To the contrary, when releasing of can 2 is required, the internal pressure of the concave is made higher than the atmospheric pressure by blowing (as shown in FIG. 1 by arrow D) by means of the flow switching device.

In the present embodiment, holding and releasing of can 2 are made by changing internal pressure of the concave by means of the flow switching device, however, the holding means is not limited to the above. Any other means, which provides for holding and releasing of can, might be adopted. For example, holding and releasing of can 2 might be made by an electromagnet which is buried in the receiving element 3.

The receiving element 3 is engaged with a shaft 7 which is rotatably extended through substrate 6, so that the element 3 is rotated together with the shaft 7.

An inspecting means 8 has a sensor 9 and a sensor holder 10 which holds the sensor 9. The number of sensor holders 10 are equal to that of cans 2 which are held thereby, and the sensor holders face surface 2a of flange of the can 2. In the present embodiment, the number of sensors 9 and that of sensor holders 10 are six each, however, any other numbers might be selected.

A locating means 11 has a cylindrical substrate 12, a cylindrical rib cam mechanism 13, and a rotary mechanism 14, wherein the substrate 12 is adjacent to the receiving element 3 and is engaged with the shaft 7, the cam mechanism sets the distance between the sensor holder 10 and a flange 2a or curl 2b of the can 2 to the prescribed value, and the rotary mechanism 14 rotatably holds the sensor holder 10.

The cylindrical rib cam mechanism 13 has a cylindrical rib cam 16 and a connecting rod 17, wherein the cylindrical rib cam 16 is formed on the substrate of the cylinder 15 near one end thereof facing the substrate 12, and one end of the connecting rod 17 is slidably connected with the cylindrical rib cam 16 and the other end is slidably engaged with a groove 12a provided in the substrate 12. The cylindrical rib cam mechanism 16 has a function which converts rotation of the shaft 7 into reciprocating movement. By the function, the sensor holder 10, which is held by the rotary mechanism 14, is moved to approach the can 2, is kept in the prescribed distance from the face of the flange of the can 2 for the prescribed period, and is then withdrawn from the can 2.

The rotation of the shaft 7 is made by a conventional driving device such as a motor (not shown). The revolutional speed of the shaft 7 is suitably settled in accordance with the production speed of a can production line. The speed is, for example, settled to 600 cans per minute in the present embodiment.

The inspection of a flanged open end part or curled open end part of a can 2 is carried out when the distance between the end of sensor holder 10, having the sensors, and the surface of the flange 2a is kept constant (hereinafter referred to as "inspection region"). The distance between the holder 10 and the flange 2a is suitably settled in accordance with the kind of can and the inspection item, for example, it is settled to 0.5 mm in the present embodiment.

The sensor holder 10 is rotated for the prescribed angle by the rotary mechanism 14 in the inspection region. The rotating angle is settled in accordance with the number of the sensors. The entire circumference of the flanged part or the entire circumference of the curled part is inspected as each sensor holder 10 is rotated.

Figure 2:
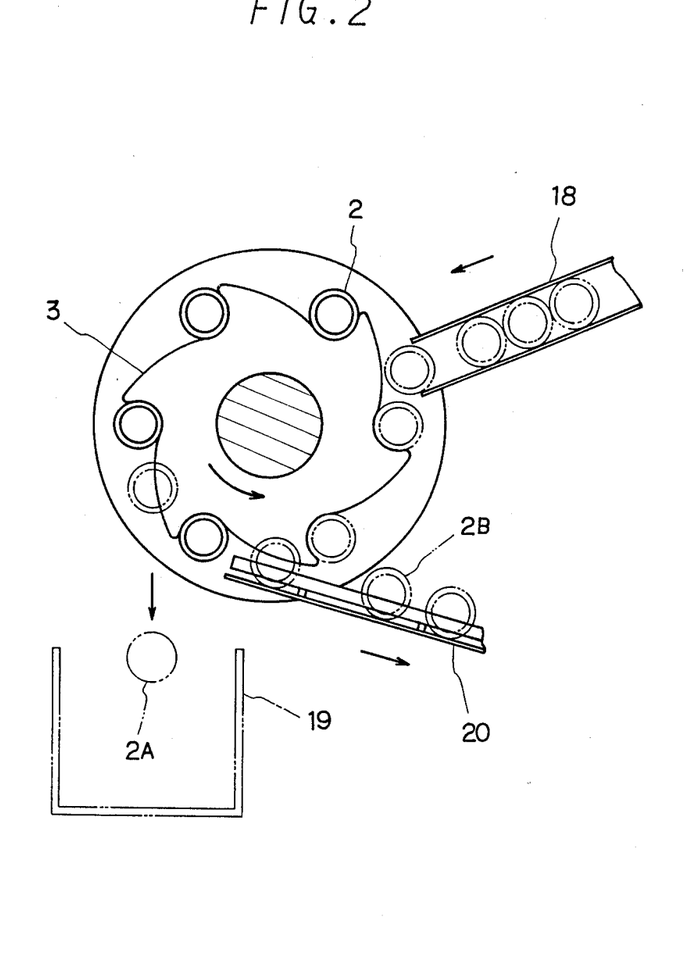
FIG. 2 shows a cross sectional view taken along the line A—A of FIG. 1.

In FIG. 2, the receiving element 3 is rotated counter-clockwise in accordance with the rotation of the shaft 7, and a can to be inspected is placed on the receiver by a feeding means 18 positioned above the right side of the receiving element 3. The receiving element 3 is formed like a ratchet wheel so that cans are placed on the receiver one by one. A can 2 positioned at the outlet of the feeding means 18 is placed on the receiver, and then the next can 2 proceeds to the outlet. However, the outlet of the feeding means is suitably closed by the receiving element 3, so that the can proceeding to the outlet of the feeding means 18 stays in it when the can 2 is placed on the receiver. Thus, the cans 2 are continuously fed into the receiving element 3.

As mentioned above, the can 2 placed on the receiver is inspected during the rotation of the receiving element 3. When any defect is detected by the inspection, the can falls into container 19 located below the left side of the receiving element 3 in the drawing (as shown in FIG. 2 by 2A). On the other hand, when no defect is detected, the can falls into a defectless can delivering apparatus 20 (as shown in FIG. 2 by 2B). Each of the cans 2 fall and is carried out by releasing the suction force, i.e., by making the pressure of the concave of the receiver positive.

Figure 3A:
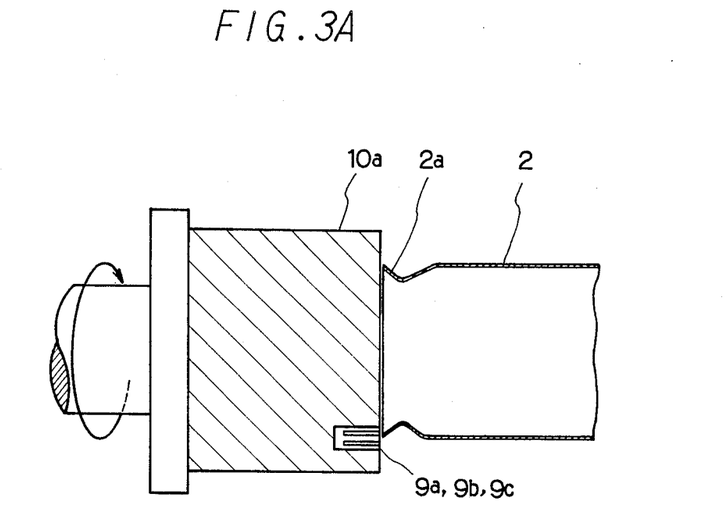
FIGS. 3A and 3B show a sectional view of a sensor holder of an embodiment of an inspection apparatus for flanged and curled open end parts of cans of the present invention.

FIG. 3A shows a can made by drawing with ironing and a sensor holder 10a for the can. Three kinds of sensors 9a, 9b and 9c are buried in the sensor holder 10a (not clearly shown in the drawing). The sensor 9a is for detecting flange crack, the sensor 9b is for checking the flange diameter, and the sensor 9C is for detecting flange gob. As mentioned above, the sensor holder 10a is controlled to be rotated a prescribed angle in the inspection region, so that the whole flange can be inspected. A sensor of an eddy current method for flaw detection and the like can be adopted as the sensor 9a, an accurate displacement detecting sensor and the like can be adopted as the sensor 9b, and an optical colour sensor and the like can be adopted as the sensor 9c.

Figure 3B:
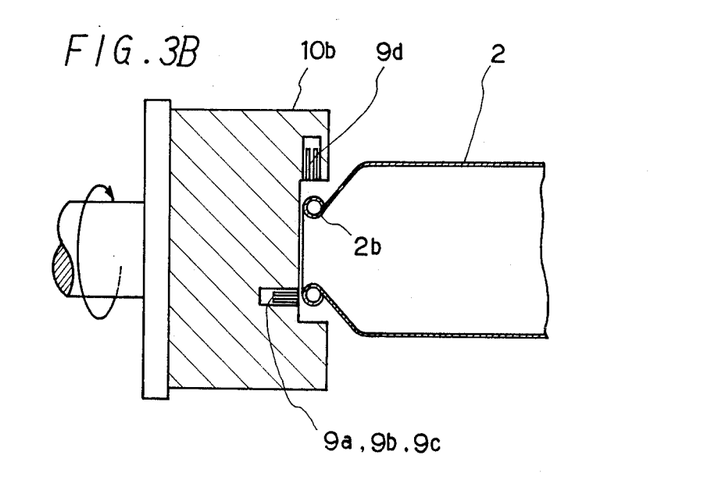

FIG. 3B shows a sensor 9d holder 10b for an aerosol can. A sensor detecting curled part defects as well as above-mentioned sensors 9a, 9b and 9c are buried in the sensor holder 10b. An eddy current method for flaw detection, an accurate displacement detecting sensor, an optical colour sensor and the like can be adopted as the sensor 9d.

The number of sensors and the kind of sensors buried in the sensor holders 10a and 10b are not limited to the above mentioned ones. The suitable kind of sensors and/or the suitable number of sensors can be selected in accordance with the kind of cans and/or inspection items. The inspection with sensors uses the theory of the eddy current method for flaw detecting which uses eddy current for detecting defects such as flaws and cracks, and the theory is well known for the person skilled in the art.

Figure 4:
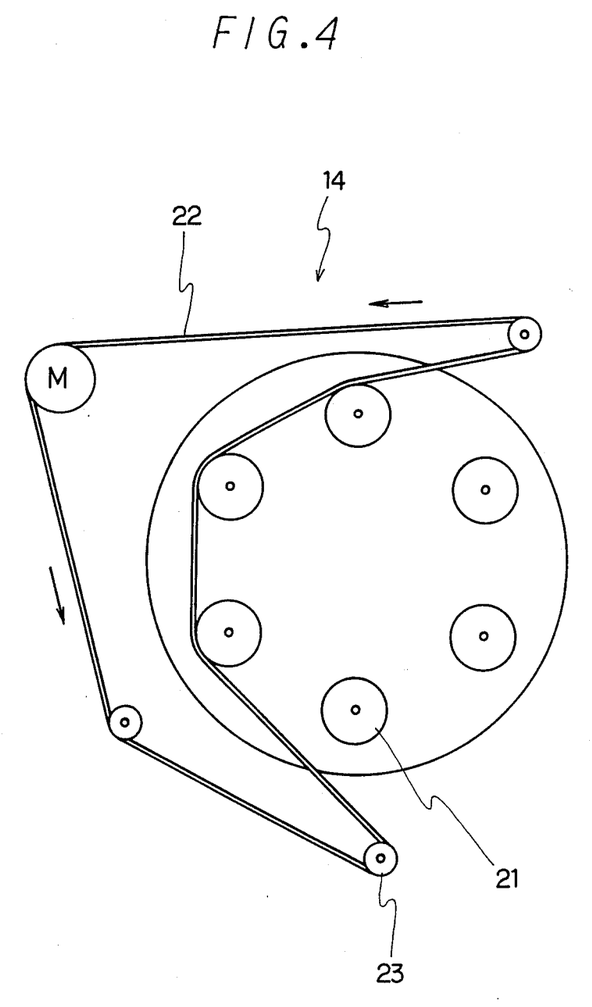
FIG. 4 shows an illustration of a rotary means for a sensor holder of the present invention.

FIG. 4 shows a rotary driving means 14 for each sensor holder 10. In the present embodiment, three sensor holders 10 are rotated by a motor M through chain 22 which is set between the motor M and a gear 21 arranged at one end of the sensor holder 10. The strength of tension of the chain 22 can be adjusted by placing a guide sprocket 23 at a suitable position.

A rotary means to rotate the sensor holder 10 is not limited to the above mentioned means. Any other conventional means such as V-belt might be adopted as a rotary means.

The number of the sensor holders 10 rotated by the rotary means 14 need not be limited to three. They can be suitably settled in accordance with the number of the sensor holders 10 and/or the number of sensors.

Figure 5:
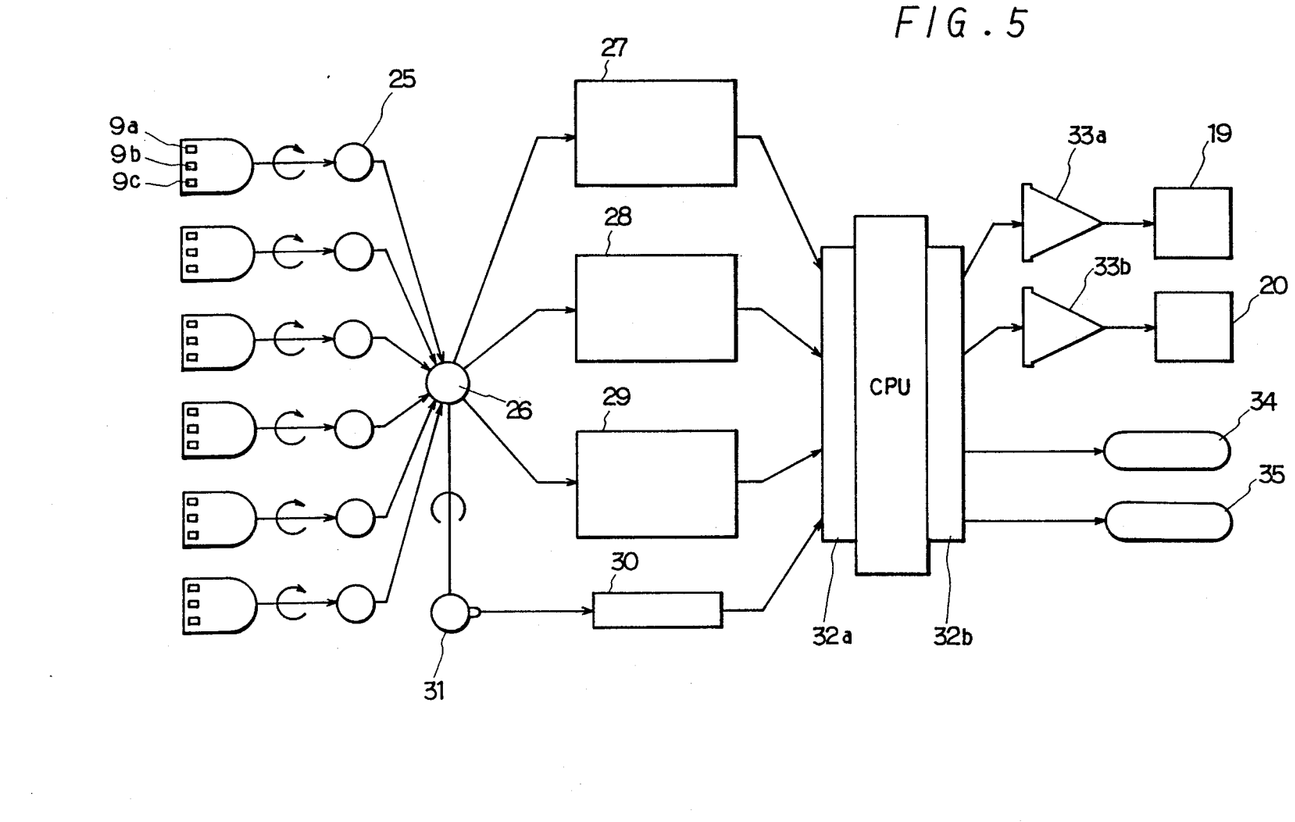
FIG. 5 shows a block diagram of an embodiment of an inspection apparatus for flanged or curled open end part of cans of the present invention.

FIG. 5 shows a block diagram of an embodiment of an inspection apparatus for flanged open end parts of cans of the present invention.

Signals from sensors 9a, 9b and 9c are transmitted to discriminating means 27, 28 and 29 respectively through slip rings 25 engaged with shaft 24 and slip rings 26 engaged with shaft 7. A six-channel eddy current device 27 and the like are adopted for detecting flange cracks, a six-channel accurate displacement sensor amplifier 28 and the like are adopted for checking flange diameters, and an optical colour discriminating sensor 29 and the like are adopted for detecting flange gobs. A similar discriminating means mentioned above is adopted for detecting curled part defects. Moreover, a processing unit 30 calculates the distance between a can and the sensors in a sensor holder 10.

The discriminating means 27, 28 and 29 discriminate if the inspected part has any defect by the level of the input signals, and then they enter the discriminated signals into a central processing unit (hereinafter referred to as CPU) through input ports 32a. The processing unit 30 enters the calculated distance between the can and the sensor by the input signal through the input port 32a.

Moreover, rotational angle of the shaft 7, i.e., the position of the can is entered into CPU by an encoder 31. The input signals from discriminating means 27, 28 and 29 and the position of the can 2 are stored at prescribed addresses in a random access memory (hereinafter referred to as RAM) of CPU. The signals stored in RAM are suitably processed by programs previously stored in a read only memory (hereinafter referred to as ROM).

Any program is acceptable for the present invention when the program has the following functions:
(a) To store the signals from the discriminating means 27, 28 and 29 for a prescribed period.
(b) To enter the suitable operating signals into a driver 33 in accordance with the stored signals when the can 2 corresponding to the stored signals reaches to the prescribed position. Namely, when the stored signals indicate that the can has any defect, it commands CPU to enter the operating signal into a driver 33a through an output port 32b, so that the can 2A having any defect falls into the container 19. On the other hand, when the stored signals indicate that the can has no defects, it commands CPU to enter the operating signal into a driver 33b through the output port 32b, so that the can 2B having no defects falls into the discharging device 20.

Moreover, a program, which is programmed to integrate the number of the cans without defects and to indicate the integrated number on an integrating indicator, might be added to the program for the production control. A program, which is programmed to send an alarm signal to an alarm display system, might be added to the program.

According to the inspection apparatus for flanged or curled open end parts of cans of the present invention, the following effects can be obtained:
(a) Visual inspection of a flanged or curled part falls into disuse.
(b) Efficiency of inspection for cans at the can production line is improved, since the inspection of the flanged or curled part is carried out continuously with plural sensors facing the can to be inspected.

While the invention has been particularly shown and described with reference to preferred embodiments thereof, it will be understood by those skilled in the art that the foregoing and other changes in form and details can be made therein without departing from the spirit and scope of the invention.

What we claim is:

1. An inspection apparatus for an open end of a can having a cylindrical body open at one end thereof comprising:
   (a) a can feeding duct from which cans are fed,
   (b) a ratchet wheel shaped can holder having a periphery facing the outlet of the can feeding duct and including means for receiving and removably holding cans fed from the can feeding duct, said can holder being rotatable about an axis and the speed of rotation of the can holder controlling the rate at which cans are fed to the can holder,
   (c) a plurality of sensor holders with each sensor holder mounting a plurality of eddy current sensors in a position facing the open end of a can to be inspected,
   (d) locating means for positioning each sensor holder at a predetermined location relative to the open end of a can to be inspected,
   (e) rotary driving means for rotating each sensor holder relative to the open end of a can being inspected,
   (f) discriminating means responsive to an output of the eddy current sensors and discriminating as to whether there is a defect in a can being inspected by the output of the eddy current sensors, and
   (g) discharge means responsive to said discriminating means and which discharges a can with a defect at a prescribed position and a can without defect at another prescribed position.

* * * * *